United States Patent [19]
Nakano et al.

[11] Patent Number: 5,635,332
[45] Date of Patent: Jun. 3, 1997

[54] ALKYLSULFONIUM SALTS AND PHOTORESIST COMPOSITIONS CONTAINING THE SAME

[75] Inventors: Kaichiro Nakano; Katsumi Maeda; Shigeyuki Iwasa; Etsuo Hasegawa, all of Tokyo, Japan

[73] Assignee: NEC Corporation, Tokyo, Japan

[21] Appl. No.: 274,436

[22] Filed: Jul. 13, 1994

[30] Foreign Application Priority Data

Jul. 14, 1993 [JP] Japan ..................... 5-174528
Jul. 14, 1993 [JP] Japan ..................... 5-174532

[51] Int. Cl.$^6$ ............. G03C 1/492; G03C 1/494; G03C 1/76; C08F 2/46
[52] U.S. Cl. .............. 430/270.1; 430/326; 430/910; 430/921; 522/31
[58] Field of Search .................. 430/270, 326, 430/921, 270.1, 910; 522/31

[56] References Cited

U.S. PATENT DOCUMENTS 5,191,124 3/1993 Schwalm et al. .................. 522/31
5,230,984 7/1993 Tachiki et al. .................. 430/270

OTHER PUBLICATIONS

T. Ueno et al., "Short Wavelength Photoresist Materials—Fine Processing for ULSI", Publisher Bunshin, 1988.

C.W. Wilkins, Jr. et al., "An organosilicon novalac resin for multilevel resist applications", *Journal of Vacuum Science and Technology*, B3(1), Jan./Feb. 1985, pp. 306–309.

Ito et al., "Applications of Photoinitiators to the Design of Resists for Semiconductor Manufacturing", *American Chemical Society Symposium Series*, vol. 242, 1984, pp. 11–23.

J. Crivello et al., "A New Preparation of Triarysulfonium . . . Selenides with Diaryliodonium Salts", *Journal of Organic Chemistry*, vol. 43, No. 15, 1978, pp. 3055–3058.

Neenan et al., "Chemically Amplified Resists: A Lithographic Comparison of Acid Generating Species", *Proceedings of SPIE*, vol. 1086, 1989, pp. 2–10.

Ueno et al., "Chemical Amplification Positive Resist Systems Using Novel Sulfonates as Acid Generators", *Proceedings of PME '89*, Kohdansha Co., 1990, pp. 413–424.

Takechi et al., "Alicyclic Polymer for ArF and KrF Excimer Resist Based on Chemical Amplification", *Journal of Photopolymer Science and Technology*, vol. 5, No. 3, 1992, pp. 439–446.

D. N. Kevill et al., "Essentially Solvent–Independent . . . and $N_{KL}$ Solvent Nucleophilicity Scale", *Journal of the American Chemical Society*, vol. 108, No. 7, 1986, pp. 1579–1585.

G. L. Gaines, Jr., "Solvatochromic Compound as and Acid Indicator in Nonaqueous Media", *Analytical Chemistry*, vol. 48, No. 2, Feb. 1976, pp. 450–451.

Primary Examiner—George F. Lesmes
Assistant Examiner—Bernard P. Codd
Attorney, Agent, or Firm—Sughrue, Mion, Zinn, Macpeak & Seas

[57] ABSTRACT

A photoresist composition containing an alkylsulfonium salt compound represented by the following general formula (I):

$$R^2-\underset{Y^-}{\overset{\overset{R^1}{|}}{S^+}}-R^3 \quad (I)$$

wherein $R^1$ and $R^2$ may be the same or different, each being a linear, branched or cyclic $C_1$ to $C_8$ alkyl radical, $R^3$ is a linear, branched or cyclic $C_1$ to $C_8$ alkyl radical, a $C_5$ to $C_7$ 2-oxocycloalkyl radical, or a linear or branched $C_3$ to $C_8$ 2-oxoalkyl radical, and $Y^-$ represents a counter ion. The photoresist composition has high transparency to deep U.V. light having wavelengths of 220 nm or less and is capable of forming good fine patterns with high sensitivity, thus being useful as chemically amplified type resist which is exposed to the deep U.V. light from an ArF excimer laser.

4 Claims, 2 Drawing Sheets

ALKYLSULFONIUM SALTS AND PHOTORESIST COMPOSITIONS CONTAINING THE SAME

BACKGROUND OF THE INVENTION

1. Field of the Invention

The present invention relates to a novel alkylsulfonium salt and a novel photoresist composition containing the same or other alkylsulfonium salt, and in particular to a novel alkylsulfonium salt in which deep ultraviolet (hereinafter "U.V."); light having a wave-length of 220 nm or less is absorbed and which efficiently generates photoacids (i.e. protonic acids), and in addition to a novel photoresist composition which contains the same or other alkylsulfonium salt and is suitable for exposure to deep U.V. light having a wavelength of 220 nm or less.

2. Disclosure of the Related Art

Recently, in the field of semiconductor devices, integrated circuits and the other various electronic devices in which fine processing has been required, photoresists have been extensively used, and highly densified and integrated devices have increasingly been desired. Thus, requirements for photolithography technology, which is used to achieve fine patterning, have become increasingly strict.

Such fine patterning has been performed by using a light exposure having shorter wavelengths to pattern of the photoresist. In general, resolution (line width) R in an optical system is defined in terms of Rayleigh's equation:

$$R = k \cdot \lambda / NA$$

wherein $\lambda$ represents a wavelength of a light source for exposure, NA represents numerical aperture of the lens and k represents a process factor. It is seen from this equation that higher resolution, i.e. a small R value, is attained by shortening the wavelength $\lambda$ of the exposure light in a photolithography. For instance, in manufacturing a dynamic random access memory (hereinafter referred to as "DRAM") having a level of integration up to 64M, resolution of the minimum pattern size 0.35 µm line-and-space has been required and for this reason, a g-line (438 nm) or i-line (365 nm) of a high-pressure mercury vapor lamp has been used as a light source to date. However, in manufacturing a DRAM having an integration level of of 256M or more, in which even finer processing techniques (processing size of 0.25 µm or less) are required, it is believed that light having shorter wavelengths, such as deep U.V. light, and excimer laser beams (KrF: 248 nm, KrCl: 222 nm, ArF: 193 nm, $F_2$: 157 nm) can be effectively used, as taught in T. Ueno et al., Short Wavelength Photoresist Materials-Fine Processing for ULSI, Publisher Bunshin, 1988. In particularly, KrF lithography is presently being actively investigated.

With regard to photoresists, high integration has been investigated on the basis of multilayer (two or three layers) resist processes in place of conventional single-layer resist processes. As for the two-layer resists, there are known, for instance, resists (two-layer resists having silylated novolak resin as the upper layer) described in Wilkins et al., Journal of Vacuum Science and Technology, B3, 306–309, 1985.

With regard to resist materials for use in fine processing, requirements for high sensitivity to exposure light increase in addition to high resolution corresponding to reduction in the processing size. This is based on the fact that it is necessary to realize improvement in the laser's cost performance because the gas life of the excimer laser light source is short and the laser itself is expensive. In order to attain high sensitivity of the resist to light, chemically amplified type resists, in which a photoacid generator is utilized as a photosensitizer, have been developed and investigated in detail as resists for use in the KrF excimer laser, as described in H. Ito and C. Grant Willson, American Chemical Society Symposium Series, Vol. 242, pp. 11–23, 1984. A photoacid generator means a material for generating an acid by light irradiation. In the chemically amplified type resist containing the photoacid generator, a protonic acid generated by the photoacid generator is moved to the solid phase of the resist in the course of a post-exposure baking treatment and thus, amplifies catalytically chemical change in the resist material several hundred times to several thousand times. This resist attains remarkably high sensitivity as compared with conventional resist having photoreaction efficiency below 1 (reaction efficiency per one photon). As for the photoacid generator for use in chemically amplified type resist, there were known, for instance, triphenylsulfonium salt derivatives described in J. V. Crivello et al., Journal of the Organic Chemistry, Vol.43, No.15, pp.3055–3058, 1978; 2,6-dinitrobenzyl esters described in T. X. Neenan et al., Proceedings of SPIE, Vol.1086, pp.2–10, 1989; and 1,2,3-tri (methanesulfonyloxy)benzene described in T. Ueno et al., Proceedings of PME'89, Kohdansha Co., pp.413–424, 1990.

Most of the resists under development at the present time are such chemically amplified type resists. The development of high photosensitive materials corresponding to exposure sources with shortened wavelengths is essentially performed by using the chemical amplification mechanism.

A chemically amplified type resist for exposure to light from the KrF excimer laser needs transmittance of 60% or more per 1 µm in thickness. In such a resist, the transmittance at the exposure wavelength is important to resolve the pattern.

However, even if the chemically amplified type single-layer resist for exposure to the g-line, i-line or KrF excimer laser beams, which is broadly used at the present time, is exposed to the light having wavelengths shorter than 220 nm (for instance, to the ArF excimer laser beams (193 nm)), generally the pattern cannot be resolved because of very strong absorption of the light to the resist. Namely, in the single-layer resist having a thickness of about 0.7–1.0 µm, the exposure light is mostly absorbed to the resist in the vicinity below its surface at the incident side of the light and, thus the light almost does not reach a portion of the resist near the substrate. As a result, the portion of the resist near the substrate is almost not exposed to light and thus the patterns are not resolved. For this reason, in photolithography in which an ArF excimer laser is the light source of the next generation following the KrF excimer laser, existing resists are not exposed to light and thus patterns are not quite resolved. The conventional photoacid generators, including Crivello et al.'s triphenylsulfonium salt derivatives which are contained in the chemically amplified type resist as mentioned above, greatly absorb exposure light having wavelengths of 220 nm or less, because all these compounds have an aromatic ring in their structure. For the above-mentioned reason, existing photoacid generators cannot be applied to chemically amplified type resists which are exposed to exposure light having wavelengths of 220 nm or less, with which higher resolution of the pattern can be expected.

With regard to a polymer to be used as the base of the resist, there are the same problems as in the photoacid generator. The polymers such as novolak resin which is used in most of the existing resists for i-line and poly(p- vinylphenol) and which is broadly used at the present time as a basic polymer of the chemically amplified type resist for exposure to the KrF excimer laser beam, have an aromatic ring in their molecular structure. This is based on the fact that it is necessary to include a number of strong unsaturated bonds in the molecular structure of the resist in order to attain sufficient resistance of the resist to a dry etching process, following the patterning process, in a method of fabricating the semiconductor device. Thus, the aromatic ring was included in the polymer for the resist as necessary and as an indispensable structure for sufficiently attaining the intended object. As mentioned above, the requirements for fine processing have become increasingly strict and further reduction in size of the pattern has been investigated. As for the resist using the KrF excimer laser as the light source having shorter wavelengths than in the i-line, poly (p-vinylphenol) has been broadly used in place of novolak resin having strong absorption at 248 nm. This resin is transparent to the KrF excimer laser beam (248 nm) (transmittance is on the order of about 70% when the film thickness is 1 μm), but has strong absorption at the wavelength region shorter than 248 nm because of the aromatic ring included in its structure. Thus, the resin cannot be utilized as the resist for lithography in which light of shorter wavelengths than in KrF, in particular light having wavelengths of 220 nm or less, is used as the exposure light. As for resin which is transparent at the wavelength region of 220 nm or less, there is a methacrylic resin, for instance, poly(methyl methacrylate) or the like. Although polymers which do not have an aromatic ring in their molecular structure exhibit transparency to light of 220 nm or less, such polymers exhibit no resistance to the above dry etching process and, as a result, cannot be utilized as the photoresist. In order to solve this problem, there is provided, resist comprising an allcyclic polymer, as reported in Takechi et al., Journal of Photopolymer Science and Technology, Vol.5, No.3, pp.439–446, 1992. In the report, a copolymer of poly(adamantyl methacrylate) and poly(tert-butyl methacrylate) has been proposed as a polymer having transparency to light at 193 nm and dry etching resistance.

As mentioned above, polymers for use in lithography which is carried out at wavelengths of 220 nm or less were reported in a few publications, but the photoacid generator which can be combined with these polymers and is necessary and indispensable to develop a chemical amplification action essential for improving the in cost performance of the laser has not been reported in any publication.

SUMMARY OF THE INVENTION

Accordingly, an object of the present invention is to provide a novel chemically amplified type photoresist composition containing an alkylsulfonium salt compound as a photoacid generator, which has high transparency to deep U.V. light of 220 nm or less and high photoreaction efficiency (high photoacid generation efficiency).

Another object of the present invention is to provide a novel photoacid generator having less absorption to deep U.V. light of 220 nm or less and high photoreaction efficiency (high photoacid generation efficiency).

According to one aspect of the present invention, there is provided a chemically amplified type photoresist composition containing an alkylsulfonium salt compound having the following general formula (I):

wherein $R^1$ and $R^2$ may be the same or different, each being a linear, branched or cyclic $C_1$–$C_8$ alkyl radical, $R^3$ is a radical selected from the group consisting of a linear, branched or cyclic $C_1$–$C_8$ alkyl radical, a $C_5$–$C_7$ 2-oxocycloalkyl radical and linear or branched $C_3$–$C_8$ 2-oxoalkyl radical; and $Y^-$ represents a counter ion.

In the above general formula (I), $R^1$, $R^2$ and $R^3$ may be the same or different. In these substituents, the linear, branched and cyclic $C_1$–$C_8$ alkyl radicals include, for instance, methyl, ethyl, n-propyl, i-propyl, n-butyl, i-butyl, sec-butyl, tert-butyl, pentyl, hexyl, heptyl, octyl, cyclopentyl, cyclohexyl, cycloheptyl, cyclopropylmethyl, 4-methylcyclohexyl and cyclohexylmethyl radicals. In $R^3$, the $C_5$–$C_7$ 2-oxocycloalkyl radical includes, for instance, 2-oxocyclopentyl, 2-oxocyclohexyl and 2-oxocycloheptyl radicals, and the linear and branched $C_3$–$C_8$ 2-oxoalkyl radicals include, for instance, 2-methyl-2-oxoethyl, 2-ethyl-2-oxoethyl, 2-isopropyl-2-oxoethyl and 2-hexyl-2-oxoethyl radicals.

As for $R^1$ and $R^2$, the above-mentioned radicals are generally effective and at least one of $R^1$ and $R^2$ is preferably the cyclic alkyl radical which provides excellent thermal stability (i.e., the starting temperature of thermal decomposition is high) and a high melting point.

As for $R^3$, the above-mentioned radicals are generally effective and the linear, branched and cyclic 2-oxoalkyl radicals are preferred as they provide such very high photoreaction efficiency (i.e. high photoacid generation efficiency).

$Y^-$ includes, for instance, the counter ions such as $BF_4^-$ (tetrafluoroborate ion), $AsF_6^-$ (hexafluoroarsenate ion), $SbF_6^-$ (hexafluoroantimonate ion), $PF_6^-$ (hexafluorophosphate ion), $CF_3SO_3^-$ (trifluoromethanesulfonate ion), $Cl^-$ (chlorine ion), $Br^-$ (bromine ion), $I^-$ (iodine ion), $ClO_4^-$ (perchloric ion), and $CH_3SO_3^-$ (methanesufonate ion). It is preferred that $Y^-$ is $BF_4^-$, $AsF_6^-$, $SbF_6^-$, $PF_6^-$ or $CF_3SO_3^-$ ion in order to suppress contamination with impurity ions in the course of fabricating integrated circuits, and suppress scattering and disappearance of protonic acid from the resist in the course of post exposure baking treatment, which is applied to form the resist patterns.

The alkylsulfonium salt derivatives of general formula (I) of the present invention can be prepared, for instance, according to a D. N. Kevill et al.'s method relating to the preparation of sulfonium salts described in the Journal of the American Chemical Society, Vol.108, No.7, pp. 1579–1585, 1986. Namely, an excess of halogenated alkyl represented by the following general formula (II) or (III):

or

wherein $R^1$ and $R^2$ are as defined above and W represents a halogen atom such as iodine, bromine, or chlorine, is added to a solution of a sulfide derivative represented by the following general formula (IV) or (V):

or $$R^3-S-R^2 \quad (V)$$

wherein $R^1$, $R^2$ and $R^3$ are as defined above, in a solvent. The mixture is allowed to react at room temperature for 0.5–5 hours, preferably for 1–2 hours. Then, a solution of a metal salt of an organic acid represented by the following general formula (VI):

$$M^+ Y^- \quad (VI)$$

wherein $M^+$ represents $K^+$, $Na^+$ or $Ag^+$ and $Y^-$ is as defined above, in nitromethane, is added to the reaction mixture; the amount of the organic metal salt being equal in molarity to the sulfide derivative. The mixture is allowed to react at room temperature to 50° C. for 3 to 24 hours. Thereafter, insoluble metal salts are removed from the reaction mixture by filtration. The filtrate is concentrated and then poured into a bulk of poor solvent, such as diethyl ether, to reprecipitate a crude product. The precipitate thus obtained is recrystallized from a suitable solvent, such as ethyl cellosolve acetate, to obtain a final alkylsulfonium salt derivative (formula (I)).

The solvent for the sulfide derivative includes, for instance, nitromethane. The amount of halogenated alkyl to be used is generally 2 to 10 times the molarity of the sulfide derivative and preferably 5 to 20 times.

The photoacid generator, i.e. triphenylsulfonium trifluoromethanesulfonate (hereinafter referred to as "TPS"), which was developed for use in the KrF excimer laser lithography by J. V. Crivello et al. and described in the above-mentioned article, cannot be used as a constituent ingredient of the resist for use in the ArF excimer laser lithography, because the photoacid generator has very remarkable light absorption at the deep U.V. light region of 220 nm or less. In comparison with TPS, all the above-mentioned sulfonium salt derivatives for use in the present invention have, remarkably, less absorption at the deep U.V. light region of 185.5 to 220 nm. Thus, it is apparent that the sulfonium salt derivatives for use in the present invention can be used as a constituent ingredient of a resist for use in ArF excimer laser lithography from the standpoint of transparency to the exposure light. It is confirmed that the protonic acid is generated by irradiating the alkyl-sulfonium salt derivatives in the present invention with radiation such as deep U.V. light, or excimer laser beams.

The photoresist composition of the present invention comprises the alkylsulfonium salt compound, polymer and solvent as constituent elements.

In the photoresist composition of the present invention, which contains the alkylsulfonium salt compound represented by the general formula (I), the alkylsulfonium salt compound may be used alone or in combination (i.e. as a mixture of two or more). In the photoresist composition of the present invention, the content of the alkylsulfonium salt compound represented by the general formula (I) is ordinarily 0.1 to 40 parts by weight and preferably 1 to 25 parts by weight, based on 100 parts by weight of all solid content including the compound. If the content of the alkylsulfonium salt is less than 0.1 parts by weight, sensitivity to light is remarkably reduced and thus, it is difficult to form the pattern. In addition, if the alkylsulfonium salt content is beyond 40 parts by weight, it is difficult to form a uniform coating film and, scum is easily produced after development.

The polymer serving as the constituent element of the present invention can be selected from polymers having high transparency at the deep U.V. light region of 220 nm or less and having any functional group and any radical unstable to acid. For instance, it is possible to use polymers represented by the following general formula (VII):

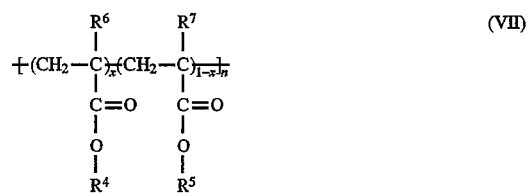

wherein n is a positive integer of 5 to 1,000, preferably 10 to 200; $R^4$ represents a tricyclodecanyl, tricyclodecenyl, tricyclodecenyloxyethyl, cyclohexyl, norbornyl or adamantyl radical as shown in Table 1; $R^5$ represents a methyl, ethyl, propyl, tert-butyl, tetrahydropyranyl or 3-oxocyclohexyl radical; x is 0.1 to 1, preferably 0.2 to 0.7; $R^6$ and $R^7$ may be the same or different and represent hydrogen or a $C_1$ to $C_3$ lower alkyl radical, such as methyl, ethyl or propyl radical.

TABLE 1

| $R^4$ | Chemical Structure of Radical |
|---|---|
| Tricyclodecanyl Radical | |
| Tricyclodecenyl Radical | |
| Tricyclodecenyloxy-ethyl Radical | $-CH_2CH_2-O-$ |
| Cyclohexyl Radical | |
| Norbornyl Radical | |
| Adamantyl Radical | |

Furthermore, it is possible to use a polymer mixture containing a plurality of polymers of the above formula (VII) as the constituent elements in the present invention.

A solvent to be used in the present invention is not particularly limited and preferably includes any organic solvent in which the elements such as the polymer; the alkylsulfonium salt are sufficiently dissolved so that a uniform coating film can be formed by application of the resulting solution according to a spin coating method. The organic solvent includes, for instance, alcohol, such as n-propyl alcohol, isopropyl alcohol, n-butyl alcohol, tert-butyl or alcohol; acetate, such as methyl cellosolve acetate, ethyl cellosolve acetate, or propyleneglycol monoethylether acetate; lactate, such as methyl lactate, or ethyl lactate; acetate, such as 2-methoxybutyl acetate or 2-ethoxyethyl acetate; pyruvate, such as methyl pyruvate or ethyl pyruvate; propionate, or such as methyl 3-methoxypropionate, ethyl 3-methoxypropionate; ketones, such as N-methyl-2-pyrrolidinone, cyclohexanone or cyclopentanone, methylethylketone; cyclic alcohol, such as cyclohexanol or cyclopentanol; or ethers, such as 1,4-dioxane, ethylene glycol monomethyl ether, ethylene glycol monomethyl ether acetate, ethylene glycol monoethyl ether, ethylene glycol monoisopropyl ether, diethylene glycol monomethyl ether or diethylene glycol dimethyl ether. Of course, the solvent for use in the present invention is not limited to the above-mentioned solvents, namely all the organic solvents in which the constituent elements of the composition of the present invention are sufficiently dissolved and which are capable of forming the film, can be used to attain the object of the present invention.

The photoresist composition of the present invention comprises basically the above-mentioned alkylsulfonium salt compound, polymer and solvent, but the other elements such as a surfactant, colorant (dye, pigment), stabilizer, coating modifier and/or crosslinking agent may be added to the composition according to need.

In addition, as for a developing solution in the fine patterning process using the photoresist composition of the present invention, any appropriate organic solvent or its combined solvent or an alkali solution or aqueous alkali solution having appropriate alkali concentration can be selected according to solubility of the polymer used in the present invention therein. The organic solvent to be used is not particularly limited and includes, for instance, ketones, such as acetone or methylethylketone; alcohol, such as methyl alcohol, ethyl alcohol isopropyl alcohol; or ethers, such as tetrahydrofuran, dioxane; or a mixture thereof. The alkali solution to be used is not particularly limited and includes, for instance, a solution or an aqueous solution containing an inorganic alkali, such as sodium hydroxide, potassium hydroxide, sodium silicate, or ammonia; an organic amine, such as ethylamine, propylamine, diethylamine, dipropylamine, trimethylamine or triethylamine; or an organic ammonium salt, such as tetramethylammonium hydroxide, tetraethylammonium hydroxide, trimethylhydroxymethylammonium hydroxide, triethylhydroxymethylammonium hydroxide or trimethylhydroxyethylammonium hydroxide; or a mixture thereof.

According to another aspect of the present invention, there is provided a novel alkylsulfonium salt compound as mentioned below.

Among the above-mentioned alkylsulfonium salt compounds represented by the general formula (I), the compounds of the formula (I),in which $R^1$ and $R^2$ may be the same or different, $R^1$ is a linear, branched or cyclic $C_1$-$C_8$ alkyl radical; $R^2$ is a $C_5$ to $C_7$ cycloalkyl radical; $R^3$ is a $C_5$-$C_7$ 2-oxo-cycloalkyl radical; and $Y^-$ is as defined above, are novel and have less absorption of deep U.V. light having wavelengths of 220 nm or less and effectively generate the protonic acid, as mentioned above.

In these novel alkylsulfonium salt compounds, the linear, branched and cyclic $C_1$ to $C_8$ alkyl radicals and $C_5$ to $C_7$ 2-oxocycloalkyl radical include, for instance, the radicals as defined above. The $C_5$ to $C_7$ cycloalkyl radical includes, for instance, a cyclopentyl, cyclohexyl, cycloheptyl, 4-methylcyclohexyl or cyclohexylmethyl radical as mentioned above.

The novel alkylsulfonium salt compounds in the present invention include, for instance, the following compounds:

cyclohexylmethyl(2-oxocyclohexyl) sulfonium trifluoromethanesulfonate;

dicyclohexyl(2-oxocyclohexyl)sulfonium trifluoromethanesulfonate;

cyclopentylmethyl(2-oxocyclohexyl)sulfonium trifluoromethanesulfonate; and cycloheptylmethyl(2-oxocyclopentyl)sulfonium trifluoromethanesulfonate.

Of course, the novel alkylsulfonium salt compounds are prepared in the same manner as mentioned above and have the same light absorption as mentioned above, and also generate the protonic acid in the same manner as mentioned above.

Thus, these novel compounds can be utilized as an initiator of cationic photopolymerizaton using light having short wavelengths and as a sensitizer for a photoresist as discussed above. Of course, the photoresist compositions containing these compounds are prepared in the same manner as mentioned above.

In each of the above-mentioned substituents in these novel compounds, the number of carbon atom is selected as is practical and an approximately similar effect can be attained even if the carbon atom number is beyond the above values, this is so for instance, even if the number of carbon atoms is 9 or more in $R^1$ and 3–4 and 8 or more in $R^2$ and $R^3$.

In the present invention, when the coating film obtained from the photoresist composition is exposed to deep U.V. light from an ArF excimer laser, the compound of general formula (I), including the novel compound which is contained in the exposed portion of the coating film, generates the acid according to the following reaction scheme (VIII):

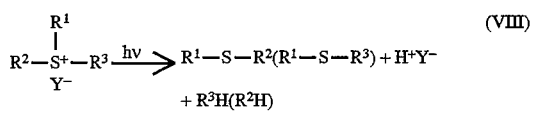

wherein $R^1$, $R^2$, $R^3$ and $Y^-$ are as defined in the general formula (I).

In the present invention, for instance, if the polymer represented by general formula (VII) wherein $R^5$ is a tert-butyl radical is used, the protonic acid generated by light irradiation brings about chemical change in the tert-butyloxy radical in the polymer according to the following reaction scheme (IX) to form a carboxylic group and 2-butene and thus, induces change in the solubility of the resist.

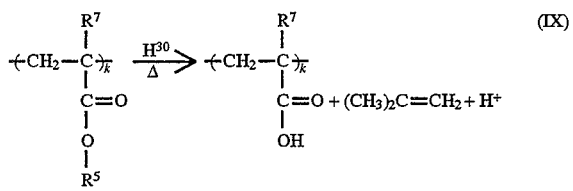

wherein k is a positive integer and $R^7$ is as defined in general formula (VII).

If post exposure baking following exposure to light is carried out at any prescribed temperature, this elimination reaction of a protective group takes place catalytically and thus, sensitivity is amplified. The polymer in which the functional group changed to the hydroxyl group according to this reaction is soluble in alkali. Thus, the polymer flows out by using an alkaline developing solution and as a result, the exposed portion is dissolved to form a positive type pattern.

As discussed in the following Examples, it was confirmed that the protonic acid was generated by irradiating the above-mentioned alkylsulfonium salt with deep U.V. light, such as the ArF excimer laser beams having a wavelength of 193 nm.

Furthermore, if the photoresist composition of the present invention is applied as shown in the Examples, it was confirmed from resolution experiments using, for instance, the ArF excimer laser beams as the exposure light, that a good rectangular fine pattern was formed with high sensitivity.

Namely, the composition containing the alkylsulfonium salt derivative in the present invention as the constituent element can be utilized as a photoresist for forming fine patterns in a lithography, in which deep U.V. light having wavelengths of 220 nm or less is used as the exposure light.

The foregoing and other objects and features of the present invention will be apparent from the following description.

DETAILED DESCRIPTION OF THE PREFERRED EMBODIMENTS

Figure 1:
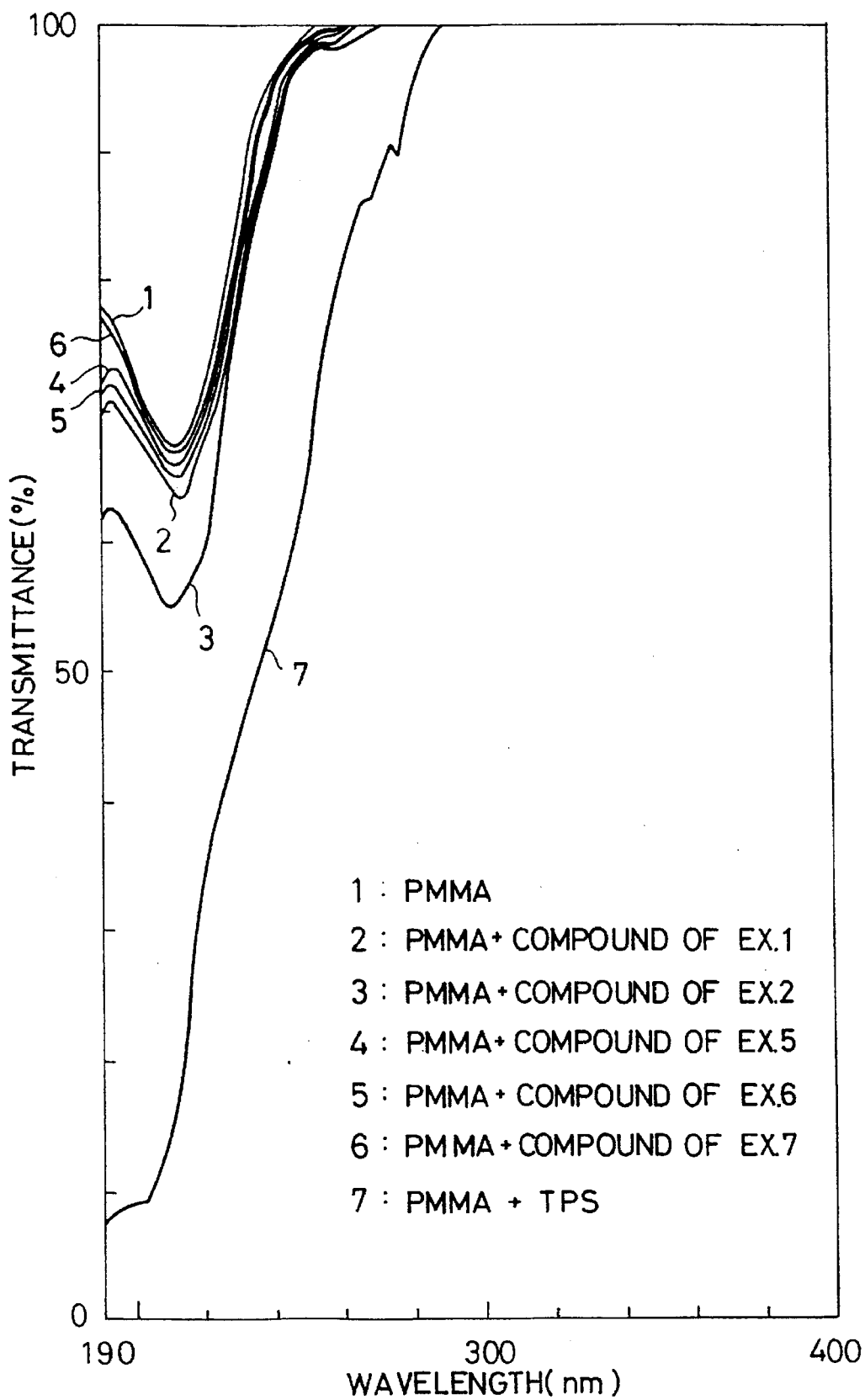
FIG. 1 is a diagram showing dependence of transmittance of each of seven films obtained in Example 8 (film-forming materials: compounds of Examples 1, 2, 5, 6 and 7; PMMA; and PMMA+TPS) on wavelength which was determined using an ultraviolet visible spectrophotometer.

The present invention will be hereinafter described in more detail with reference to the non-limiting working Examples and the effects practically achieved by the present invention will also be discussed in more detail in comparison with the Control Example.

EXAMPLE 1

Preparation of cyclohexylmethyl(2-oxocyclohexyl) sulfonium trifluoromethanesulfonate:

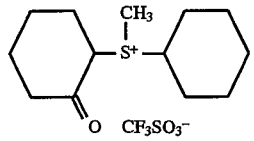

The following preparation was carried out under a yellow lamp.

10.0 g (41.1 mmol) of 2-(cyclohexylmercapto)cyclohexanone was dissolved in 30 ml of nitromethane in a 300 ml round bottomed glass flask and stirred with a Teflon stirring bar/magnetic stirrer. To the solution, 54 g (380 mmol) of methyl iodide was added with a dropping funnel and, at the end of dropping, stirred at room temperature for one hour. Then, to the resulting solution, a solution of 12.1 g (41.1 mmol) of silver trifluoromethanesulfonate in 200 ml of nitromethane was gradually added dropwise with a dropping funnel. After stirring for 15 hours, deposited/silver iodide was separated by filtration and the nitromethane solution was concentrated to 20 ml. The nitromethane solution thus concentrated was poured into 200 ml of diethyl ether to precipitate a crystal. The crystal thus deposited was washed with diethyl ether several times and thereafter the residue was recrystallized from ethyl cellosolve acetate to obtain 11.2 g(yield: 63%) of a final product. The structure of the final product was identified by a $^1$H-NMR measurement (an AMX-400 type NMR apparatus manufactured by Bruker Co.), an IR measurement (IR-470 manufactured by Shimadzu Co.) and elemental analysis. Thermal analysis was performed by a Thermal Analysis System 001 (Mack Science Co.).

Melting Point: 91°–93° C. $^1$H-NMR (CDCl$_3$, internal standard: tetramethylsilane): δ (ppm) 1.22–1.35(m, 1H), 1.40–1.78(m, 6H), 1.84–2.27(m, 8H), 2.54–2.64(m, 2H), 2.70–2.80(m, 1H), 2.81(s, 1.5H), 2.92 (s, 1.5H), 3.62(tt, 0.5H), 3.73(tt, 0.5), 5.17(t, 0.5H), 5.18(t, 0.5H)

IR (KBr tablet, cm$^{-1}$) 2950, 2870($v_{C-H}$), 1710($v_{C=O}$), 1450($v_{C-H}$), 1276, 1256($v_{C-F}$), 1148, 1034($v_{SO_3}$)

Elemental Analysis:

|  |  | C | H | S |
|---|---|---|---|---|
| Found | (% by weight): | 44.43 | 6.38 | 16.84 |
| Calculated | (% by weight): | 44.67 | 6.16 | 17.03 |

(The calculated values are based on C$_{14}$H$_{23}$O$_4$S$_2$F$_3$(MW: 376.4485))

Starting Temperature of Thermal Decomposition: 142° C.

EXAMPLE 2

Preparation of dicyclohexyl(2-oxocyclohexyl)sulfonium trifluoromethanesulfonate:

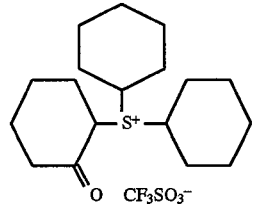

In this Example, the same procedures as used in Example 1 were repeated to synthesize a desired final product, except that methyl iodide was replaced with cyclohexyl iodide. The yield of the final product was 13%. The structure of the final product was identified by the same analysis method as in Example 1.

Melting Point: 172°–174° C. $^1$H-NMR (CDCl$_3$, internal standard: tetramethylsilane): δ (ppm) 0.97–2.3(m, 24H), 2.33–2.80(m, 4H), 3.97–4.47(m, 2H), 5.20–5.35(m, 1H)

IR (KBr tablet, cm$^{-1}$) 2932, 2860($v_{C-H}$),1700($v_{C=O}$), 1444($v_{C-H}$),1276, 1256($v_{C-F}$),1168, 1050($v_{SO_3}$)

Elemental Analysis:

|  |  | C | H | S |
|---|---|---|---|---|
| Found | (% by weight): | 51.58 | 6.75 | 14.74 |
| Calculated | (% by weight): | 51.33 | 7.03 | 14.42 |

(The calculated values are based on C$_{19}$H$_{31}$O$_4$S$_2$F$_3$(MW: 444.5667))

Starting Temperature of Thermal Decomposition: 185° C.

EXAMPLE 3

Preparation of cyclopentylmethyl 2-oxocyclohexyl) sulfonium trifluoromethanesulfonate:

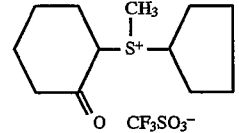

In this example, the same procedures as in Example 1 were repeated to synthesize a desired final product, except that 2-(cyclohexylmercapto)cyclohexanone was replaced with 2-(cyclopentylmercapto)cyclohexanone. The yield of the final product was 93% and it was oily. The structure of the final product was identified by the same analysis method as in Example 1.

$^1$H-NMR (CDCl$_3$, internal standard: tetramethylsilane): δ (ppm) 1.50–2.50(m, 14H), 2.51–2.80(m, 2H), 2.85(s, 1.5H), 2.95(s, 1.5H), 3.67–4.23(m, 1H), 4.87–5.37(m, 1H)

IR (KBr tablet, cm$^{-1}$) 2950, 2880($v_{C-H}$), 1710($v_{C=O}$), 1448, 1424($v_{C-H}$), 1264($v_{C-F}$), 1156, 1030($v_{SO_3}$)

Elemental Analysis:

|  |  | C | H |
|---|---|---|---|
| Found | (% by weight): | 43.02 | 5.65 |
| Calculated | (% by weight): | 43.08 | 5.79 |

(The calculated values are based on C$_{13}$H$_{21}$O$_4$S$_2$F$_3$(MW: 362.4217))

EXAMPLE 4

Preparation of cycloheptylmethyl(2-oxocyclopentyl) sulfonium trifluoromethanesulfonate:

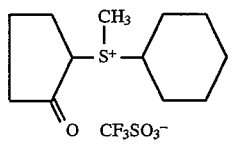

In this example, the same procedures as in Example 1 were repeated to synthesize a desired final product, except that 2-(cyclohexylmercapto)cyclohexanone was replaced with 2-(cycloheptylmercapto)cyclopentanone. The yield of the final product was 20%. The structure of the final product was identified by the same analysis method as in Example 1.

Melting Point: 97°–99° C.

Elemental Analysis:

|  |  | C | H |
|---|---|---|---|
| Found | (% by weight): | 44.20 | 6.21 |
| Calculated | (% by weight): | 44.67 | 6.16 |

(The calculated values are based on C$_{14}$H$_{23}$O$_4$S$_2$F$_3$(MW: 376.4485))

EXAMPLE 5

Preparation of dimethyl (2-oxocyclohexyl)sulfonium trifluoromethanesulfonate:

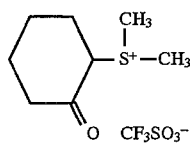

In this example, the same procedures as in Example 1 were repeated to synthesize a desired final product, except that 2-(cyclohexylmercapto)cyclohexanone was replaced with 2-(methylmercapto)cyclohexanone. The yield of the final product was 96% and it was, oily. The structure of the final product was identified by the same analysis method as in Example 1.

$^1$H-NMR (CDCl$_3$, internal standard: tetramethylsilane): δ (ppm) 1.47–2.83(m, 8H), 2.92(s, 3H), 3.02(s, 3H), 4.70–5.30 (m, 1H)

IR (KBr tablet, cm$^{-1}$) 3032, 2988($v_{C-H}$), 1710($v_{C=O}$), 1450, 1428($v_{C-H}$), 1264($v_{C-F}$), 1160, 1030($v_{SO_3}$)

Elemental Analysis:

|  |  | C | H |
|---|---|---|---|
| Found | (% by weight): | 35.46 | 5.23 |
| Calculated | (% by weight): | 35.06 | 4.90 |

(The calculated values are based on C$_9$H$_{15}$O$_4$S$_2$F$_3$(MW: 308.3303))

EXAMPLE 6

Preparation of methylpropyl(2-oxocyclohexyl)sulfonium trifluoromethanesulfonate:

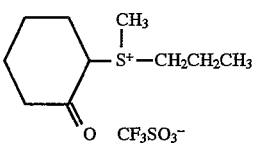

In this example, the same procedures as in Example 1 were repeated to synthesize a desired final product, except that 2-(cyclohexylmercapto)cyclohexanone was replaced with 2-(propylmercapto)cyclohexanone. The yield of the final product was 88% and it was oily. The structure of the final product was identified by the same analysis method as in Example 1.

$^1$H-NMR (CDCl$_3$, internal standard: tetramethylsilane): δ (ppm) 1.13(t, 1.5H), 1.14(t, 1.5H), 1.65–2.05(m, 5H), 2.08–2.25(m, 2H), 2.57–2.71(m, 3H), 2.87(s, 1.5H), 2.97(s, 1.5H), 3.19–3.40(m, 2H), 5.13–5.18(m, 1H)

IR (KBr tablet, cm$^{-1}$) 2940, 2880($v_{C-H}$), 1710($v_{C=O}$), 1448, 1424($v_{C-H}$), 1260($v_{C-F}$), 1156, 1030($v_{SO_3}$)

Elemental Analysis:

|  |  | C | H |
|---|---|---|---|
| Found | (% by weight): | 39.55 | 5.86 |
| Calculated | (% by weight): | 39.28 | 5.69 |

(The calculated values are based on C$_{11}$H$_{19}$O$_4$S$_2$F$_3$(MW: 336.3839))

Referential Example 1

Preparation of dicyclohexylmethylsulfonium trifluoromethanesulfonate:

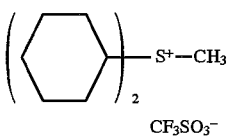

In this example, the same procedures as in Example 1 were repeated to synthesize a desired final product, except that 2-(cyclohexylmercapto)cyclohexanone was replaced with dicyclohexylsulfide. The yield of the final product was 73%. The structure of the final product was identified by the same analysis method as in Example 1.

Melting Point: 52°–54° C.

$^1$H-NMR (CDCl$_3$, internal standard: tetramethylsilane): δ (ppm) 1.07–2.40(m, 20H), 2.82(s, 3H), 3.37–3.97(m, 2H)

IR (KBr tablet, cm$^{-1}$) 2940, 2860($v_{C-H}$), 1446($v_{C-H}$), 1261($v_{C-F}$), 1148, 1030($v_{SO_3}$)

Elemental Analysis:

|  |  | C | H |
|---|---|---|---|
| Found | (% by weight): | 46.65 | 6.86 |
| Calculated | (% by weight): | 46.39 | 6.95 |

(The calculated values are based on $C_{14}H_{25}O_3S_2F_3$(MW: 362.4649))

Starting Temperature of Thermal Decomposition: 164° C.

EXAMPLE 8

Transmittance measurement on a resin film containing an alkylsulfonium salt:

Film-forming procedures and resolution experiments as described below were carried out under a yellow lamp.

1.5 g of poly(methyl methacrylate) having a weight-average molecular weight of 12,000 which was manufactured by Aldrich Chemical Company (hereinafter referred to as "PMMA") and 0.079 g of the alkylsulfonium salt which was prepared in Examples 1, 2, 5, 6 or 7 were dissolved in 6 g of ethyl cellosolve acetate and filtered through a membrane filter having 0.2 µm pore size. The resulting filtrate was spin-coated on a 3-inch quartz (silica) substrate and the spin coated film thus formed was baked on a hot plate at 100° C. for 120 seconds. Thus, there were obtained five kinds of thin films each having a thickness of around 1 µm. Dependence of transmittance of the thin films thus obtained on wavelength was determined using an ultraviolet visible spectrophotometer of the UV-365 type, which was manufactured by Shimadzu Co. The results are shown in FIG. 1.

For comparison with these films, a film of PMMA alone and a film in which the above alkylsulfonium salt was replaced with a known triphenylsulfonium trifluoromethanesulfonate compound (hereinafter referred to as "TPS") were prepared in the same manner as mentioned above. Measured spectra on the films under the same conditions are also shown in FIG. 1.

It can be seen from this example that the TPS-containing PMMA film has extremely reduced transmittance at the wavelength region of 220 nm or less whereas the films containing the alkylsulfonium salts of the Examples of the present invention have high transmittance and thus, the alkylsulfonium salts of the present invention are an effective to material for chemically amplified resists for use in lithography, in which the exposure wavelength is not more than 220 nm.

EXAMPLE 9

The amount of photoacid generated from an alkylsulfonium salt in acetonitrile was irradiated with ArF excimer laser beams (193 nm) and its efficiency was measured as discussed below.

First, 0.3 ml of a solution of the alkylsulfonium salt of Example 1 or TPS in acetonitrile ($1\times10^{-2}$ mol·l$^{-1}$) was put in a synthesized quartz cell having a cell length of 1 mm (GL Science Co.). Then, the cell was irradiated with ArF excimer laser beams (HE-460-SM-A type excimer laser manufactured by NEC Co.) at room temperature (exposure area: 3 cm$^2$). After irradiation, the exposed solution was added to an acetonitrile solution containing sodium salt of tetrabromophenol blue as an indicator. Visible light absorption spectra were measured on the resulting solution. The amount of acid thus obtained was determined on the basis of change in absorbance at 619 nm according to the method described in the Analytical Chemistry, Vol. 48, No. 2, 450–451 (1976), the disclosure of which is hereby incorporated by reference herein. The measured results are shown in the following Table 2.

TABLE 2

| Photoacid Generator | Amount of Acid Generated (nmol)* | Quantum Yield |
|---|---|---|
| Compound of Example 1 | 67.4 | 0.348 |
| TPS | 48.8 | 0.249 |

*Exposure amount: 40 mJ · cm$^{-2}$

It can be seen from the above results that the alkylsulfonium salt of the present invention is effective as a photoacid generator.

EXAMPLE 10

The amount of photoacid generated from an alkylsulfonium salt-containing PMMA film (film thickness of 1.0 µm), which was irradiated with ArF excimer laser beams (193 nm), and its efficiency were measured as discussed below.

As for the photoacid generator, the alkylsulfonium salts of Examples 1 to 7 were used. The amount of each of the alkylsulfonium salts to be used was 5 wt. % based on PMMA. Each of thin films, which were formed on a 3-inch silicon wafer in the same manner as in Example 8, were irradiated with ArF excimer laser beams having a center wavelength of 193.3 nm (EX-700 manufactured by Lumonics Co.). In this case, the exposure amount was 40 mJ·cm$^{-2}$ and the exposure area was 20 cm$^2$. After irradiation, the respective thin films were dissolved in acetonitrile. The respective solutions were added to an acetonitrile solution containing a sodium salt of tetrabromophenol blue as an indicator and then visible light absorption spectra were measured on the respective solutions. The amount of acid thus generated was determined on the basis of change in absorbance at 619 nm, according to the method described in Analytical Chemistry, Vol.48, No.2, 450–451 (1976), as mentioned in Example 9. With regard to the relation between the molar number of acid and absorbance, calibration was previously made from absorbances of the known amounts of p-toluenesulfonic acid and the acetonitrile solution as an indicator, and the calibration curve was used in the determination of the acid. The measured results are shown in the following Table 3.

TABLE 3

| Photoacid Generator | Amount of Acid generated (nmol) |
|---|---|
| Example 1 | 14.0 |
| Example 2 | 2.0 |
| Example 3 | 13.2 |
| Example 4 | 13.5 |
| Example 5 | 10.9 |
| Example 6 | 11.0 |
| Referential Example 1 | 1.0 |

Referential Example 1

It can be seen from the above results that the alkylsulfonium salts in the present invention are effective as a photoacid generator. In particular, it is believed that the ketone group (2-oxocycloalkyl group) structure in the alkylsulfonium salt compound dramatically enhances the photoacid generation efficiency due to deep ultraviolet light, such as produced by ArF excimer laser beams. Thus, the alkylsulfonium salt compound having such a ketone group is more preferable.

Referential Example 2

Preparation of poly(tricyclo[5.2.1.0$^{2,6}$]decanyl methacrylate-co-tert-butyl methacrylate):

10 ml of a solution of 2,2'-azobis(isobutyronitrile) 0.48 g (0.003 mol) in toluene was added to 120 ml of a toluene solution of tricyclo[5.2.1.0$^{2,6}$]decanyl methacrylate 21.80 g (0.10 mol) and tert-butyl methacrylate 8.80 g (0.05 mol). Thereafter, these monomers were subjected a polymerization reaction at 70° C. for one hour. After the temperature of the reaction mixture was returned to room temperature, the reaction mixture was poured into 1 liter of methanol. The precipitate was recovered by sucking filtration and it was washed with methanol. After the washing and filtration procedures were repeated three times, the precipitate thus recovered was dried under reduced pressure to obtain 14.52 g (yield: 48.4%) of poly(tricyclo[5.2.1.0$^{2,6}$]decanyl methacrylate-co-tert-butyl methacrylate), as a white powder. The tricyclo[5.2.1.0$^{2,6}$]decanyl methacrylate unit and tert-butyl methacrylate unit in the final product was in the ratio of 65:35. This copolymerization ratio was determined on the basis of $^1$H-NMR measurements. The product had a weight-average molecular weight of 53,000 (on a polystyrene basis) which was determined on the basis of GPC measurements.

EXAMPLE 11

An ArF contact exposure experiment using a photo-resist composition according to the present invention:

The following experiment was carried out under a yellow lamp.

Figure 2A:
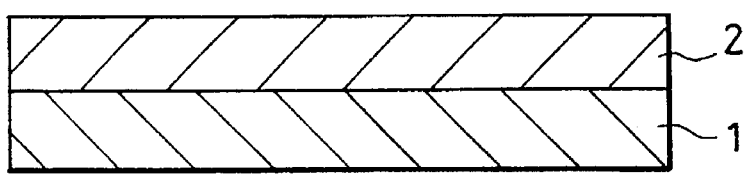
FIGS. 2A to 2C show a series of partial and schematical cross-sectional views to explain a process for forming a positive type pattern using a photoresist composition of the present invention.
Figure 2B:
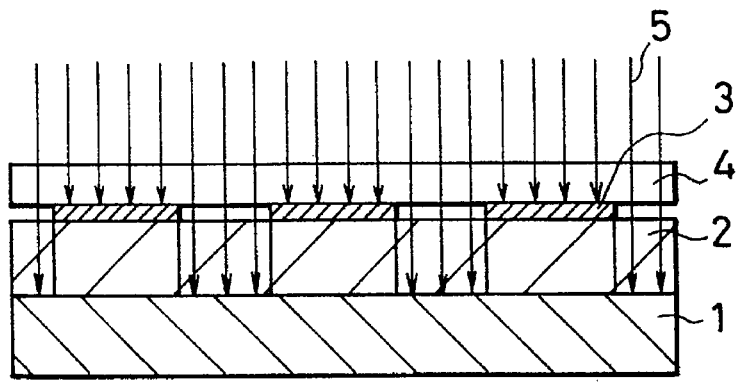
Figure 2C:
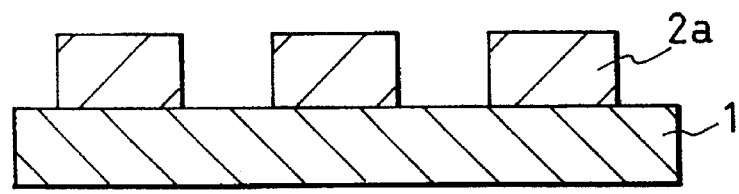
Figure 3:
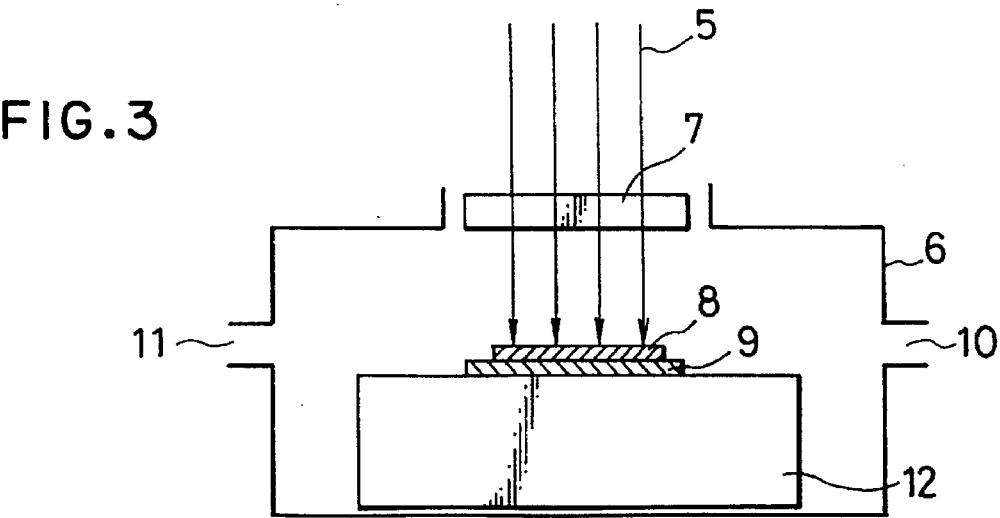
FIG. 3 shows a schematic illustration of a simple laboratory light exposure apparatus as used in the exposure experiment described in Example 9.

First, a resist material comprising the following composition was prepared:
(a) poly(tricyclo[5.2.1.0$^{2,6}$]decanyl methacrylate-co-tert-butyl methacrylate) (resin: the polymer of Referential Example 1): 2.85 g
(b) cyclohexylmethyl(2-oxocyclohexyl)sulfonium trifluoromethanesulfonate (photoacid generator: the compound of Example 1): 0.15 g
(c) cyclohexanone (solvent): 12.00 g The above mixture was filtered through a 2 μm Teflon filter to prepare the resist material. A method of forming a pattern will be described below with reference to FIGS. 2A to 2C and 3. FIGS. 2A to 2C show a series of partial and schematical cross-sectional views of a process for forming a positive type pattern by using a photoresist composition of the present invention and FIG. 3 shows a schematic illustration of a simple laboratory light exposure apparatus to be used in this Example. The laboratory light exposure apparatus comprises a glove box (6), a homogenizer (7) provided on the top of the glove box through which the exposure light is introduced, a nitrogen intake vent (10) and a nitrogen exhaust vent (11) which are provided on side walls of the glove box, and a X-Y stage (12) for placing and fixing a substrate (1) (a wafer (9)) which is placed in the glove box.

Referring now to FIG. 2A, the above resist material was spin-coated on a 3-inch silicon substrate (1) and then baked on a hot plate at 90° C. for 60 seconds to form a thin resist film (2) having a thickness of 0.7 μm. The thin resist film (2) exhibited a high transmittance of 73.2% per 1 μm thick and thus, it can be said that the transparency of the film is as high as a single-layer resist. Then, as shown in FIG. 3, a wafer (9) consisting of the substrate (1) and the thin resist film (2) formed thereon, was placed and fixed on the X-Y stage (12) in the simple laboratory light exposure apparatus, which was thoroughly purged with nitrogen. Thereafter, as shown in FIG. 3, a mask (8) with a pattern of a chromium member (3) formed on a quartz (silica) plate member (4) was adhered onto the surface of the thin resist film (2) of the wafer (9) and the thin resist film (2) was irradiated through the mask (8) with ArF excimer laser beams (5). As shown in FIG. 2B, the quartz plate member (4) (a transmitting portion) of the patterned mask (8) transmits the laser beams (5) and the chromium member (3) (a portion for cutting off the laser beams) of the patterned mask (8) cuts off the laser beams (5) to protect the thin resist film located therebelow. At the end of irradiation, the thin resist film (2) was baked on a hot plate at 100° C. for 90 seconds, was developed in an alkaline developing solution (an aqueous solution of 2.0 wt. % tetra-methylammonium hydroxide) of 23° C. for 30 seconds and then rinsed for 60 seconds in purified water. As a result, only the portion of the resist film exposed to the beams was dissolved in the developing solution and removed therefrom to form the positive type pattern 2a as shown in FIG. 2C.

In the above-mentioned experiment, the resolution property of 0.25 μm line-and-space was obtained when the exposure energy was around 68.5 mJ/cm$^2$.

EXAMPLES 12 to 18

The same procedures as in Example 11 were repeated to prepare seven resist materials, except that the compound of Example 1 as the photoacid generator was replaced with each of the alkylsulfonium salt compounds obtained in Examples 2 to 7 and 1-adamantyldimethylsulfonium trifluoromethanesulfonate, and patterns were formed in the same manner as in Example 11. The experimental conditions and results are shown in Table 4.

The content of the photoacid generator in each of the resist materials is enough to resolve the patterns, which is based on the photoacid generation efficiency as shown in Example 10, i.e. an amount of photoacid generated by the same exposure amount. Namely, the amount of the photoacid generator having lower photoacid generation efficiency was more than that of the other photoacid generator having higher photoacid generation efficiency.

TABLE 4

| Ex. | Acid Generator | Amount of Acid Generator (g) | Amount of Resin (g) | Exposure Amount (mJ · cm$^{-2}$) | Resolution (μm L&S) |
|---|---|---|---|---|---|
| 12 | Example 2 | 0.60 | 2.40 | 75.4 | 0.40 |
| 13 | Example 3 | 0.18 | 2.82 | 70.0 | 0.25 |
| 14 | Example 4 | 0.18 | 2.82 | 69.5 | 0.25 |
| 15 | Example 5 | 0.21 | 2.79 | 88.4 | 0.25 |
| 16 | Example 6 | 0.21 | 2.79 | 87.2 | 0.30 |
| 17 | Referential Example 1 | 0.60 | 2.40 | 88.5 | 0.50 |
| 18 | AdMe$_2$* | 0.45 | 2.15 | 88.7 | 0.45 |

*AdMe$_2$ is 1-adamantyldimethylsulfonium trifluoromethane-sulfonate prepared according to the method described in D. N. Kevill and S. M. Anderson, J. Am. Chem. Soc., 108, 1579–1585 (1986) and has the following formula:

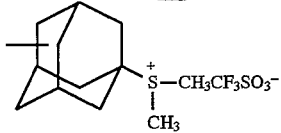

As discussed above, the photoresist composition containing the alkylsulfonium salt according to the present invention has high transparency to radiation, such as deep U.V. light having a wavelength region of 220 nm or less, and further exhibits high sensitivity and resolution. Thus, the resist composition is useful as a photoresist which is exposed to light, such as deep U.V. light of 220 nm or less. Furthermore, by using the photoresist composition according to the present invention, it is possible to form the fine or densified patterns required to fabricate a semiconductor device.

Furthermore, the novel alkylsulfonium salt in the present invention has high transparency to radiation, such as deep U.V. light having wavelength of 220 nm or less, and further effectively generates a protonic acid by exposing of the compound to radiation, as mentioned above. Thus, the compound is useful as a photosensitizer (i.e. photoacid generator) for use in a photoresist for deep U.V. light, particularly, light of a wavelength of 220 nm or less.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A photoresist composition comprising
(a) an alkylsulfonium salt compound represented by the following general formula (I):

wherein $R^1$ and $R^2$ each are a radical selected from the group consisting of methyl, ethyl, n-propyl, i-propyl, n-butyl, i-butyl, sec-butyl, tert-butyl, pentyl, hexyl, heptyl, octyl, cyclopentyl, cyclohexyl, cycloheptyl, cyclopropylmethyl, 4-methylcyclohexyl, and cyclohexylmethyl radicals, $R^1$ and $R^2$ may be the same or different; $R^3$ is a radical selected from the group consisting of 2-oxocyclopentyl, 2-oxocyclohexyl, and 2-oxocycloheptyl radicals; and $Y^-$ is a counter ion selected from the group consisting of $CF_3SO_3^-$, $ClO_4^-$, and $CH_3SO_3^-$; and (b) a polymer wherein said polymer has transparency under ultraviolet radiation of 220 nm or less and has a functional group or a radical which is unstable to acid.

2. A photoresist composition as claimed in claim 1, wherein $R^2$ is a radical selected from the group consisting of cyclopentyl, cyclohexyl, cycloheptyl, 4-methylcyclohexyl, and cyclohexylmethyl radicals.

3. A photoresist composition as claimed in claim 1, wherein said polymer is represented by the following general formula (VII):

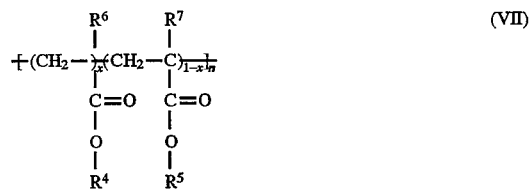

wherein n is a positive integer of 5 to 1,000; $R^4$ is a radical selected from the group consisting of tricyclodecanyl, dicyclopentenyl, dicyclopentenyloxyethyl, cyclohexyl, norbornyl, and adamantyl radicals; $R^5$ is a radical selected from the group consisting of methyl, ethyl, propyl, tert-butyl, tetrahydropyranyl, and 3-oxocyclohexyl radicals; x is 0.1 to 1; and $R^6$ and $R^7$ may be the same or different and are selected from the group consisting of a hydrogen atom, a methyl radical, an ethyl radical, and a propyl radical.

4. A photoresist composition as claimed in claim 1, wherein said alkylsulfonium salt compound is in an amount of 0.1 to 40 parts by weight based on 100 parts by weight of all solid content of said composition.

* * * * *